(12) United States Patent  
Schuller

(10) Patent No.: US 8,757,154 B2
(45) Date of Patent: Jun. 24, 2014

(54) AIR PURIFIER APPARATUS

(76) Inventor: Carmen Schuller, New York, NY (US)

( * ) Notice: Subject to any disclaimer, the term of this patent is extended or adjusted under 35 U.S.C. 154(b) by 74 days.

(21) Appl. No.: 13/295,835

(22) Filed: Nov. 14, 2011

(65) Prior Publication Data

US 2013/0037027 A1 Feb. 14, 2013

Related U.S. Application Data

(60) Provisional application No. 61/521,535, filed on Aug. 9, 2011.

(51) Int. Cl.
*A62B 7/10* (2006.01)

(52) U.S. Cl.
USPC .......... 128/205.12; 128/204.18; 128/205.27

(58) Field of Classification Search
USPC .......... 128/201.25, 204.18, 204.21, 205.12, 128/205.22, 205.27–206.12, 206.18
See application file for complete search history.

(56) References Cited

U.S. PATENT DOCUMENTS

| | | | |
|---|---|---|---|
| 4,051,893 A | 10/1977 | Guibert | |
| 4,494,538 A * | 1/1985 | Ansite | 128/205.25 |
| 4,971,609 A | 11/1990 | Pawlos | |
| 5,265,592 A * | 11/1993 | Beaussant | 128/201.24 |
| 6,536,429 B1 | 3/2003 | Pavlov et al. | |
| 6,866,041 B2 | 3/2005 | Hardy, Jr. et al. | |
| 2003/0154983 A1 | 8/2003 | Marx | |
| 2005/0126572 A1 | 6/2005 | Gosweiler | |
| 2007/0000492 A1* | 1/2007 | Hansel et al. | 128/204.23 |
| 2008/0127979 A1* | 6/2008 | Becker et al. | 128/205.27 |
| 2008/0308106 A1* | 12/2008 | Augustine et al. | 128/205.29 |
| 2010/0263672 A1* | 10/2010 | Acharya | 128/206.11 |
| 2011/0030689 A1 | 2/2011 | Wilkinson et al. | |
| 2011/0056496 A1* | 3/2011 | Tilley et al. | 128/205.27 |
| 2012/0138058 A1* | 6/2012 | Fu et al. | 128/204.23 |

* cited by examiner

*Primary Examiner* — Justine Yu
*Assistant Examiner* — Valerie L Skorupa
(74) *Attorney, Agent, or Firm* — Leason Ellis LLP.

(57) ABSTRACT

The invention relates to a modular, portable, air purifier and mask device capable of supplying filtered or otherwise conditioned airflow to an individual. More specifically, the present invention provides a modular air purification system that allows for the selection of multiple types of air treatment modules, power modules and mask devices. Through selective combination of a variety of modules, a desired air quality and condition is achieved.

13 Claims, 3 Drawing Sheets

AIR PURIFIER APPARATUS

BACKGROUND OF THE INVENTION

This invention relates to a portable wearable powered air filtration, conditioning, and sterilization system.

This invention claims priority from, and herein incorporates by reference, U.S. Provisional Application 61/521,535, filed on Aug. 8, 2011.

Devices for respiratory protection are readily available for medical applications. The most common devices are negative pressure respirators which typically take the form of either a mask or a half mask respirator. In either case, the mask covers the nose and mouth and air is drawn through the filter by the negative pressure of inhalation. These types of masks increase respiratory stress because the user must overcome the air restriction presented by the air filter. A tight fit is essential to prevent unfiltered air from entering around the mask instead of through the filter. These types of masks also interfere with normal conversation because they cover both the nose and mouth.

Also available, are Powered Air Purifying Respirators (PAPRs) which use small battery operated motor and fan assemblies to draw air through the filter and supply it at a positive pressure to the user's face mask. These units eliminate respiratory stress and are not dependent on a tight fit between the face and mask. However, they also interfere with normal conversation because they are supplied with full or half masks that cover both the nose and mouth.

The problem with both these types of respirators is that they are not cosmetically appealing and are therefore seldom worn outside an industrial workplace. For example, those devices in the prior art, are not portable or unobtrusive enough to be suitable. U.S. patent to Her-Mou (U.S. Pat. No. 5,267, 557) herein incorporated by reference, is directed to providing a nose mask with a filtering device and nose clamp. The mask has been adapted to have an inlet pipe and an exhaust pipe and the air supply being driven by a dc current motor, U.S. patent to Hauff (U.S. Pat. No. 4,233,972) herein incorporated by reference, is directed to providing a battery operated filter blower unit arranged to be supported by the person, The mask has a filter unit and blower unit that can be adapted to different types of face masks. The filtered blower also has an ejection space for the diffusion of blown air. U.S. patent to Pokhis (U.S. Pat. No. 4,331,141); Vrabel (U.S. Pat. No. 5,009,225); Sibley (U.S. Pat. No. 5,848,592); Piesinger (U.S. Pat. No. 6,772,762), all of which are herein incorporated by reference, provides a head and upper torso covering devices wherein upon inhalation, air from the ambient surroundings are drawn in through a filter and passed to the user. Additionally, the inventions optionally provide for an electric motors to impel air into the apparatus.

However, there are many non-industrial situations in which respiratory protection would be highly beneficial. Allergy sufferers would greatly benefit from a pollen filter when outside during the allergy season as would people bothered by air pollution on high pollution days. Airline travelers would benefit from a cabin air ozone and germicidal filter, especially on long flights. Hospital workers and patients would benefit from germicidal filters. Finally, industrial workers would benefit from a less obtrusive respirator in non-toxic environments such as woodworking.

Although negative respirators could be worn in everyday non-industrial environments, they seldom are because of their obtrusiveness, respiratory discomfort, and difficulty in engaging in conversation. Currently available positive pressure PAPRs are large, noisy, and typically are supplied with full face masks. It would be extremely rare to see one of these units worn outside the workplace.

In summary, there are currently no acceptable devices for respiratory protection that are practical and cosmetically acceptable for use outside the industrial environment.

Figuereo, et al in U.S. Pat. No. 5,878,742, herein incorporated by reference, attempts to make a PAPR more appealing by disclosing a plenum go arrangement near the forehead of the wearer along with a baffle for distributing the air from the plenum downward over the wearer's mouth, nose, and face. However, his device is still very large and obtrusive and would not appeal to users outside the workplace. 65

The primary problem with current portable PAPRs is that they are powered by fans or blowers. Fans and blowers can only supply very low static air pressures. This requires that large diameter hoses and large surface area air filters be used so as to not overly constrict the airflow from the blower. Typical hose diameters between a belt mounted blower and the face mask are one inch or larger.

Another problem with current negative respirators and PAPRs is that they are all designed to cover both the nose and mouth. However, covering only the nose would be perfectly acceptable in many non-toxic environments. For example, an allergy sufferer breathing filtered air through the nose would not be bothered by an occasional breath of unfiltered air through the mouth.

Yet another problem with both negative respirators and PAPRs is that they are only designed to filter the air and not to sterilize or condition it.

Accordingly, it is the object of the present invention to provide a new personal positive pressure powered respiratory protection system that would be cosmetically acceptable to the average user in an everyday environment.

Another object of the invention is to provide a system that can be easily configured for different filtering situations by offering various types of air filtration, sterilization, and conditioning capabilities using standard plug-in modules. Typical types of air filtration that will be provided are particulate, odor, ozone, and selected organic and chemical vapors. Sterilization will be provided using ultra-violet germicidal lamps. Typical air conditioning provided will be heating, cooling, or moisturizing the filtered air.

Yet another object of the invention is to make the whole system portable, wearable, and concealable.

SUMMARY OF THE INVENTION

In accordance with the broad aspects of the present invention, the apparatus disclosed provides a portable air purifier capable of supplying filtered or otherwise conditioned airflow to an individual. More specifically, the present apparatus provides, in part, a modular air purification system that allows for the selection of air treatment modules and the combining of them to achieve desired air quality and characteristics.

The present device allows an individual to filter the ambient atmosphere in a way that is unobtrusive and does not require extensive machinery. Additionally the present device is compact and easily portable, allowing for ease of movement.

A further aspect of the apparatus allows a user to filter smoke, dust and other allergens so as to enable a healthier environment for those persons who are sick or of advanced illness. In the present invention, the air purifier and its connected nasal mask are light enough to be carried or worn on a variety of transportation mediums, such as airplanes, trains, and in extended car travel.

A still further aspect of the apparatus allows for the modular system to be customizable for various tasks such as air purification, sterilization, and conditioning configurations by simply plugging in different filter, conditioning or sterilization modules.

BRIEF DESCRIPTION OF THE DRAWINGS

The foregoing and other features of the present invention will be more readily apparent from the following detailed description and drawings of illustrative embodiments of the invention in which list the drawings and their captions.

DETAILED DESCRIPTION OF THE INVENTION

By way of overview and introduction, the present invention concerns an apparatus for generating a purified air for personal intimate use by an individual. The apparatus is further directed to modular personal air purifier system that is portable and discrete. Lastly, the present invention allows for a device that provides sufficient air pressure which employs the use of minimal electrical power to effectuate itself.

Figure 1:
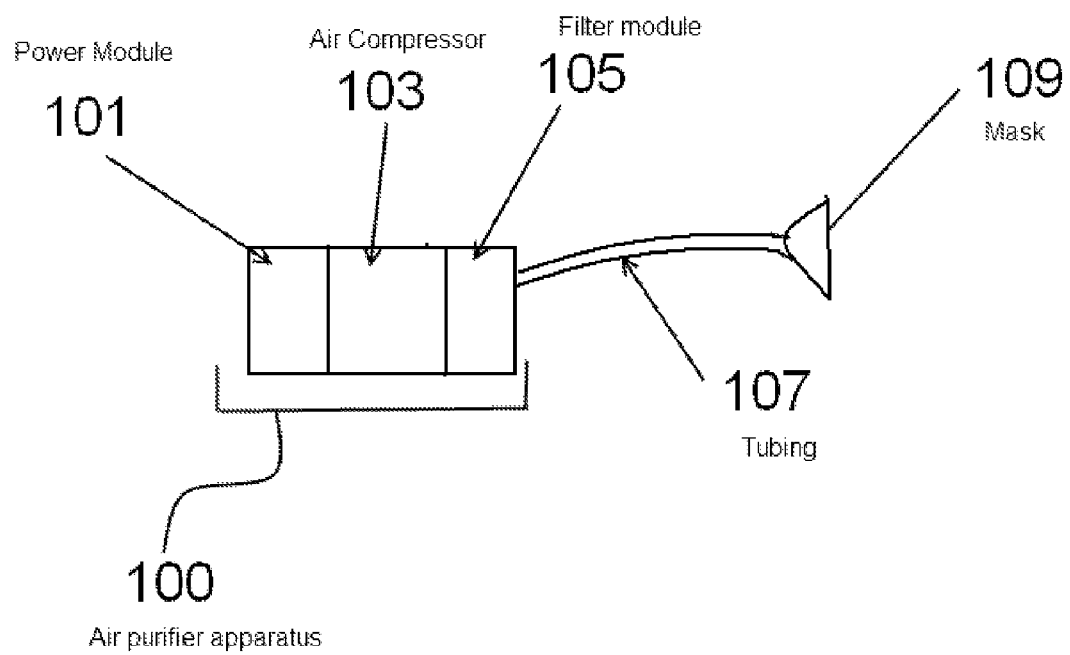
FIG. 1 is an illustrative side diagram of the components of an embodiment of the invention.

As seen in FIG. 1, the present invention provides a modular air purifier 100. The air purifier apparatus is configured to have a series of discrete physical modules that are configured to fit to one another (101-105) so as to provide all the necessary functions of a portable air purifier. In one embodiment of the device, a power pack 101 is secured to an air compressor 103. The power pack is configured as a housing, having a body of roughly cylindrical or oblong dimensions. Within this housing, an electrical energy generation means is secured, for example a battery pack. Furthermore, the power module is configured so that all necessary electrical connections are made between the compressor module 103 and the power module 101 without the need additional tools or hardware. In an embodiment of the apparatus shown, the power module 101 is provided with a series of batteries (not shown). The provided batteries are rechargeable and removable from the power module 101. Therefore, the power module 101 can be put in contact with a base station style charger, or the individual battery cells themselves can be removed. Additionally, in an alternative embodied, the power module 101 can supply direct current from a residential outlet or commercial source by employing an AC/DC converter. In an alternative embodiment, the present invention power module uses a fuel cell or other form of electrical energy generation. Additionally, in still a further embodiment, a photovoltaic cell is affixed to the body and provides either supplemental, or compete electrical power to the device. In still a further embodiment, an airplane or automobile charger can supply direct electrical power to the power module 101

The power module 101 is fitted via electrical and physical connectors to an air compression module 103. The air compression module 103 is configured to extract ambient air from the surrounding environment via vents and direct it to the user via a hose or tubing 107 to a nasal cover 109. The air compressor 103 is configured as being located within a housing of similar dimensions to that of the power pack. Those skilled in the art would readily appreciate that the dimensions described herein are in no way limited.

The present device is configured as an air compressor that is designed to function utilizing the low current and voltage supplies of batteries and other direct current power sources. The air compressor may be a custom or commercial available compressor suitable for the functions so described. Furthermore, those skilled in the art would easily recognize any necessary gearing, valves, and other air movement elements necessary for a functioning air compressor so as to be fully described. The electrical connections that provide linkages to the power module are provided within the body of the housing and are configured to direct electricity to the internal mechanism of the air compressor, for example, a brushless motor. In the provided embodiment, the air compressor module is configured to use a standard fan-bladed compressor to compress air. This air is extracted through vent openings located on the sides of the air compressor housing 103. Once air has been compressed, it is directed to the front of the device, through another vent or grate.

An alternative embodiment provides that present device employs the use of fan-less air compression devices, such the use of impellers. In a still further embodiment of the device, the air compressor can use a bladed intake fan along with induced effects from an impeller using the Coanda effect. For example, by the generation of low pressure zones around a vent and hence inducing air flow that lacks buffeting. Therefore, in those embodiments incorporating this type of air compressor, the resulting air stream is less volatile and provides for a gentler inhalation experience.

As stated previously, the body of the air compressor module can be made in similar dimensions and materials as the power unit 103. However, in the present embodiment the overall length of the air compressor module is larger than that of the power module 103. Those skilled in the art would rapidly recognize those materials and housing elements that would suitably allow for the durable construction of an air compressor, such as steel, plastics, composites and synthetic materials.

As in the embodiment of the device depicted in FIG. 1, once the air has been compressed by in the air compression module 103, the compressed air is directed to a filtering unit 105. The filtering unit 105 is configured as a modular housing having the same size and shape as the previous modules. The body of the housing posses a vent that accepts the compressed air from the air compression unit 103 and passes it through a series of removable or non-removable filters. These filters can be of any type and made suitable to restrain particulate matter in the air stream. For example it is provides that the filters can remove, dust, pollen and other allergens from the air prior to inhalation by the user. Additionally, it is possible to use electrostatic filters to remove particles, such as smoke, from the air stream. Additionally, filters with anti-bacterial, anti-microbial or anti-viral properties can be included. In an additional embodiment, the filters of the present device also include a series of filters that can be stacked so as to achieve combination of filtering mechanisms. In accordance with the outlines of the invention, it is possible to effectuate air filtering using a series of filters. For example particulate filtering provided using HEPA (high efficiency particulate air) filters. Odor and ozone filtering will be provided using activated carbon, cpz (carbon, permanganate, and zeolite), or the like. Organic and chemical vapor filtering could be provided using readily available filters custom packaged for this system. Air sterilization will be provided using an ultraviolet germicidal lamp. Air conditioning will be provided using a distilled water moisturizing module for humidifying, a solid state thermoelectric cooler module for cooling, and a resistive element for heating.

Upon filtering of the air stream, the filter module 105 directs the filtered air to a progressively narrowing cap 107 that increases the air pressure and drives the compressed air through a flexible tube 107 or conduit.

The filtered air, directed through the tube 107 is then transported to the nasal mask 109. The nasal mask 109 is configured and adapted to cover the nose of the user, but does not interfere with the mouth or eyes of the user. The nasal mask 109 is configured with an inlet that allows the tube to direct filtered and compressed air to the nose. In a particular embodiment, the nasal mask 109 is secured to the face of the user with a strap or string that wraps around the back of the skull and is secured with a clasp or tab. In an alternative embodiment, the pressed device uses negative pressure to secure the nasal mask to the face without the need of straps. In this embodiment, the nasal mask 109 contains on its surface vents 301 that are capable of opening outwards only. As such when a user exhales, the vents open and expel the user's breath. Alternatively, when the user inhales, the vents are closed, thereby producing negative pressure, which accelerates the filtered air into the user's lungs, as well as forming a air tight seal with the nasal mask.

Figure 2:
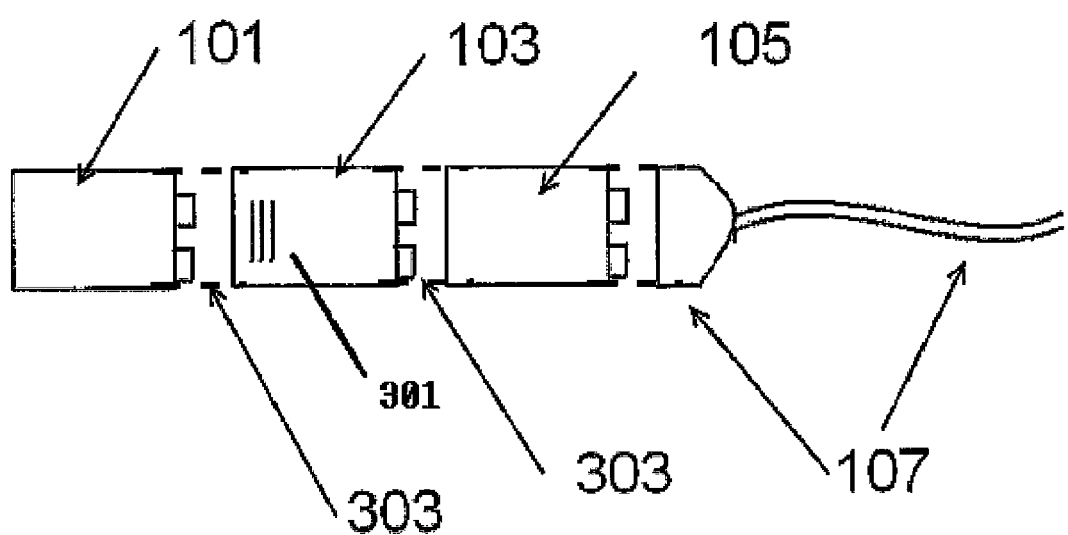
FIG. 2 is an exploded view of an embodiment of the invention.

As described above, the modules of the present device are configured to fit together with one another. Specifically, each module can be combined with other modules so that the electrical and air flow connections can be passed from one module to the next depending on the arrangement of the modules. As depicted in FIG. 2, the power module 101 connects to the air purifier 103 module by connection sockets or plugs 303. The connection sockets 303 are equipped with electrical connectors configured to mate with sockets (not shown) located on one end of the air purifier 103. These sockets provide both electrical connections, but also physically connect the modules into a single piece. Additionally, electricity as well as compressed air can be passed to the next module through similarly designed connection sockets 303. In the depicted device the filtering module is connected. In the event that a filtering module is not necessary, the compression cone and hose 107 is fitted to the top most module and is designed to ground the electrical connection and direct the compressed air. In those embodiments where the one or more filtering modules are present, the compression cone and hose 107 is simply secured to the output of the last filter.

Figure 3:
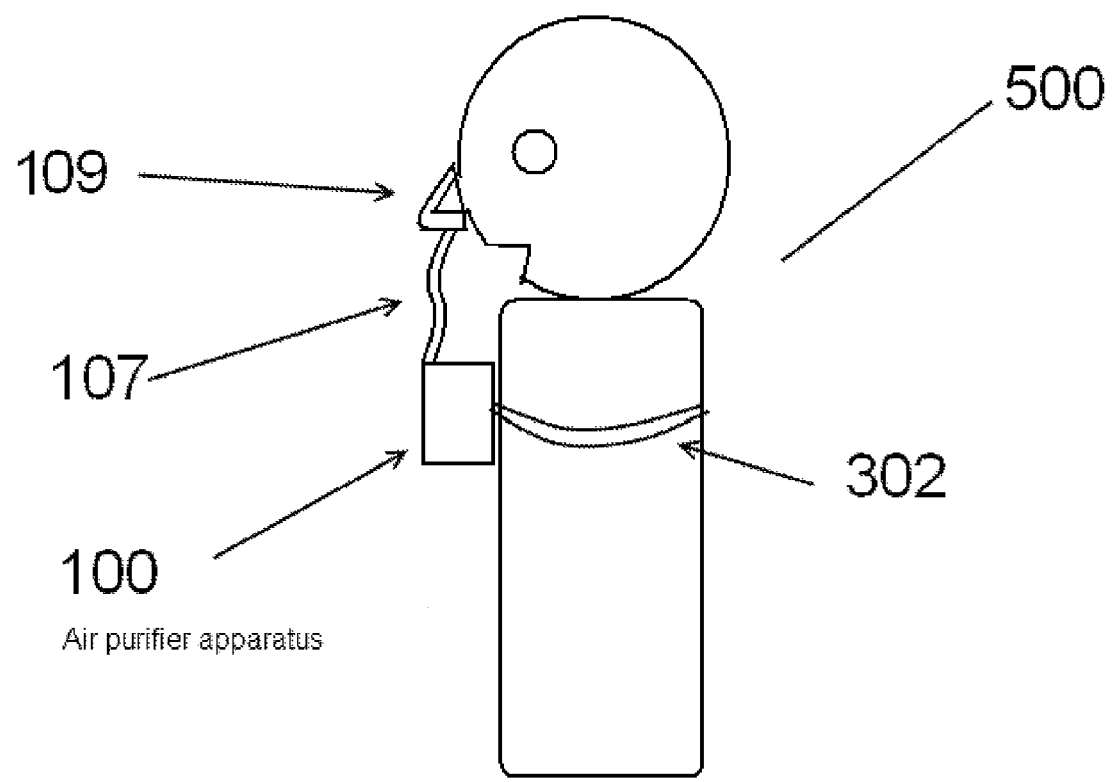
FIG. 3 is an illustrative side view of one of the embodiments.

As depicted in FIG. 3, the device described can be secured to the user 500 by means of a harness or belt 302. The belt or harness can be used to secure both the device when in operation, and also function as a storage unit for when the device is not in use, but is being carried. Additionally, the belt has portions or pouches for the storage of additional filter modules, additional power modules or other elements not herein described.

While the modules herein described are an embodiment of the device as depicted in the Figures, those skilled in the art would recognize the additional modules that could be stacked on the device in question. For example, in a non-depicted embodiment, an additional UV filter is added to the filtering stage. A humidifier module can be added in addition or in alternative to the modules already provided. In both these embodiments, the power module provides sufficient electrical power to provide proper functioning of the modules.

In the alternative arrangement of elements, the portable air purification apparatus is equipped with a second air compression module, wherein the second air compression module provides accelerated and pressurized air stream to the first air compression module.

In an additional alternative arrangement of elements the portable air purification apparatus is also equipped with an oral cavity mask configured to connect to the filtering module, this could be a separate filtering device from those envisioned as part of the apparatus. In this arrangement the oral cavity mask is configured to connect to an exhaust outlet. In an alternative arrangement, the power module is a battery pack, alternating current power supply or direct current power supply. The power supply can be computer controlled so as to be on a timer, or respond to environmental conditions and factors.

The filter module can be selectively engageable, that is the filtering functions themselves can be selectively engaged by a user manually, or via a pre-programmed routine stored within the memory of a computer. For example, ionizing radiation inserts integral to a filter module are selectively engaged for specific events or situations. Other inserts for the filter modules are envisioned.

It should be understood that various combination, alternatives and modifications of the present invention could be devised by those skilled in the art. The present invention is intended to embrace all such alternatives, modifications and variances that fall within the scope of the appended claims.

While the invention has been particularly shown and described with reference to a preferred embodiment thereof, it will be understood by those skilled in the art that various changes in form and details may be made therein without departing from the spirit and scope of the invention.

What is claimed is:

1. A portable air purification apparatus comprising:
   a power module with a common power interface;
   a first air compression module with a common air interface and a common power interface, wherein the air compression module provides a stream of air through its common air interface that substantially lacks buffeting;
   at least one filtering module with a common air interface;
   wherein the at least one filtering module, the power module and the first air compression modules are configured to connect together in series with one another so that the power module distributes electrical energy to another one of the modules through its common power interface and the another one of the modules is adapted to distribute electrical energy to a further one of the modules through its common power interface, and the at least one air compression module is configured to distribute compressed air to the at least one filtering module through their common air interfaces, wherein each of the common power interfaces and common air interfaces is configured to couple one of the modules to another of the modules; and
   a nasal mask configured to connect to the filtering module and direct compressed air into the nasal passages of a user.

2. The portable air purification apparatus of claim 1 further comprising:
   a second air compression module with a common air interface, wherein the second air compression module provides accelerated and pressurized air stream to the first air compression module through their common air interfaces.

3. The portable air purification apparatus of claim 1 further comprising:
   an oral cavity mask configured to connect to the filtering module.

4. The portable air purification apparatus of claim 3 wherein:
   the oral cavity mask configured to connect to an exhaust outlet.

5. The portable air purification apparatus of claim 4 wherein:
the exhaust outlet includes an exhaust filter.

6. The portable air purification apparatus of claim 1 wherein:
the power module is a battery pack, alternating current power supply or direct current power supply.

7. The portable air purification apparatus of claim 1 wherein:
the power module is operated via a control circuit.

8. The portable air purification apparatus of claim 7 wherein:
the control circuit is a digital or analog electrical circuit.

9. The portable air purification apparatus of claim 1 wherein:
the at least one filter module is selectively engageable, wherein the engagement is controlled by a control circuit.

10. The portable air purification apparatus of claim 9 wherein:
the control circuit is a computer configured to execute a series of instructions so as to selectively engage at least one filter module according the series of instructions.

11. The portable air purification apparatus of claim 1 further comprising:
a harness adapted to be secured to the user, wherein the harness is adapted to be secured to the user directly, or to an article of clothing worn by a user by means of a clip, fastener, hook or attachment device.

12. A portable air purification apparatus comprising:
a plurality of modules removably coupled to one another in series, wherein the air purification apparatus includes:
a power module with a common power interface wherein the power module is equipped with a computer programmable timer;
a first air compression module with a common air interface and a common power interface, wherein the air compression module provides a stream of air through its common air interface that substantially lacks buffeting;
at least one filtering module with a common air interface; wherein the at least one filtering module, the power module and the first air compression module are configured to connect together with one another so that the power module distributes electrical energy to the first air compression module through its common power interface, and the first air compression module is configured to distribute compressed air to the at least one filtering module through their common air interfaces;
a nasal mask configured to connect to the at least one filtering module and direct compressed air into the nasal passages of a user; and
an air humidity modification module with a common air interface and a common power interface connected in series with one of said at least one air compression module and at least said filtering module through their common air interfaces, and their common power interfaces.

13. The portable air purification apparatus of claim 12, further comprising:
a UV light source with a common air interface and a common power interface connected in series with said filtering module through their common air interfaces, and wherein said filtering module further includes a common power interface and the UV light source and filtering module are connected together through their common power interfaces.

* * * * *